US00PP15902P3

(12) United States Plant Patent
Hofmann

(10) Patent No.: US PP15,902 P3
(45) Date of Patent: Aug. 2, 2005

(54) NEW GUINEA *IMPATIENS* PLANT NAMED 'FISUPNIC CHERSWEET'

(50) Latin Name: *Impatiens hawkeri*
Varietal Denomination: Fisupnic Chersweet

(75) Inventor: Birgit C. Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 47 days.

(21) Appl. No.: 10/829,351

(22) Filed: Apr. 22, 2004

(65) Prior Publication Data

US 2004/0221350 P1 Nov. 4, 2004

(30) Foreign Application Priority Data

Apr. 29, 2003 (CA) ..... 03-3586

(51) Int. Cl.[7] ..... A01H 5/00

(52) U.S. Cl. ..... Plt./318

(58) Field of Search ..... Plt./318

*Primary Examiner*—Kent Bell
(74) *Attorney, Agent, or Firm*—Foley & Lardner LLP

(57) ABSTRACT

A new and distinct cultivar of New Guinea *Impatiens* plant named 'Fisupnic Chersweet', and particularly characterized by the combined features of bi-colored flowers, white to pale pink color and purple-red markings; relatively large, nearly round, flat to slightly cup-shaped flowers; flowers borne on long peduncels well above the foliage; dark-green, elliptically shaped leaves; vigorous growth, and tall, only moderately tight plant habit; and early to medium flowering response.

1 Drawing Sheet

Genus and species of the plant claimed *Impatiens hawkeri.*

Variety denomination: 'Fisupnic Chersweet'.

BACKGROUND OF THE INVENTION

The present invention comprises a new and distinct cultivar of *Impatiens,* botanically known as *Impatiens hawkeri,* and hereinafter referred to by the cultivar name 'Fisupnic Chersweet'.

'Fisupnic Chersweet' is a product of a planned breeding program that originated from a hybridization made by the inventor, Birgit C. Hofmann, in a controlled breeding program in Hillscheid, Germany, in 2000.

The female parent was the variety 'Alexis' (U.S. Plant patent application Ser. No. 09/765,324, abandoned), characterized by having bi-colored pink and red flowers, blackish-green foliage, small leaves and relatively short, compact plant habit. The male parent was a proprietary seedling, designated K00-6162-2 (unpatented), characterized by having bi-colored light pink and red colored flowers, dark green foliage, and moderately small plant habit.

'Fisupnic Chersweet' was discovered and selected as a flowering plant within the progeny of the stated cross by the inventor in April 2001 in a controlled environment in Galdar, Gran Canaria, Spain.

The first act of vegetative or asexual reproduction of 'Fisupnic Chersweet' was accomplished when cuttings were taken from the initial selection in July, 2001, in a greenhouse in Galdar, Gran Canaria, Spain, by, or under the supervision of the inventor.

Horticultural examination of plants grown from these cuttings initiated in the spring of 2002, in Hillscheid, Germany, and continuing thereafter, has demonstrated that the combination of characteristics as herein disclosed for 'Fisupnic Chersweet' are firmly fixed and are retained through successive generations of asexual reproduction.

'Fisupnic Chersweet' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green-house conditions which approximate those generally used in commercial practice.

BRIEF SUMMARY OF THE INVENTION

The following traits have been repeatedly observed and are determined to be basic characteristics of 'Fisupnic Chersweet', which in combination distinguish this *impatiens* as a new and distinct cultivar:

1. Bi-colored flowers, white to pale pink ground color and purple-red markings;
2. relatively large, nearly round, flat to slightly cup-shaped flowers;
3. flowers borne on long peduncels well above the foliage;
4. dark-green, elliptically shaped leaves;
5. vigorous growth, and tall, only moderately tight plant habit; and
6. early to medium flowering response.

Of the many commercial cultivars known to the inventor, the most similar in comparison to 'Fisupnic Chersweet' is the patented variety 'Fisimp 130' (U.S. Plant Pat. No. 13,691), and the parental variety 'Alexis'.

In comparison to 'Fisimp 130', 'Fisupnic Chersweet' has more distinct star-shaped markings on petals, while 'Fisimp 130' has almost no stripes on petals, only a large splotch on the upper petals. Additionally, 'Fisupnic Chersweet' has a somewhat more bluish hue. While the foliage appears similar, the plant habit of 'Fisupnic Chersweet' is somewhat taller than that of 'Fisimp 130'.

In comparison to 'Alexis', 'Fisupnic Chersweet' has larger leaves, lighter colored foliage, and much more vigorous growth habit.

BRIEF DESCRIPTION OF THE DRAWING

The accompanying photographic drawing shows typical flower and foliage characteristics of 'Fisupnic Chersweet' with colors being as true as possible with illustrations of this type. The photographic drawing shows a side view of a typical flowering plant of 'Fisupnic Chersweet'.

DETAILED BOTANICAL DESCRIPTION

In the following description color references are made to The Royal Horticultural Society Colour Chart (R.H.S.). The color values were determined indoors from plants growing in a green-house in May 2003, Hillscheid, Germany.

The description is based on plants which were planted as rooted cuttings in 12 cm pots in late February 2003, and then grown in the greenhouse at 16° C. minimum temperature. Most observations and measurements were made after the beginning of flowering in mid May, when the plants were about 12 weeks old.

Plant:

General appearance and form:

*Plant habit.*—Tall, mainly upright directed branches, upper surface of canopy rounded, only moderately tight plant habit; growth is indeterminate, though relatively weak after beginning of flowering.

*Height.*—19.5 cm.

*Width.*—30.7 cm.

*Number of branches.*—12.

*Length of branches.*—16–19 cm.

*Internode length.*—5.0–6.0 cm.

*Diameter of branches.*—7–9 mm.

*Stem color.*—Brown, RHS 179 A to 179 B.

*Propagation.*—Usually terminal shoot tips for cuttings.

*Rooting.*—Roots initiate in about 18 days at 22° C., from sticking to transplanting.

*Cultivation time.*—Producing a marketable flowering plant in a 12 cm pot takes about 10 weeks of growing time.

Foliage:

*Leaf arrangement.*—Primarily in whorls.

*Shape of leaf.*—Elliptic, with acute base and acuminate tip, surface glossy and somewhat rugose.

*Margin.*—Slightly serrated, ciliated.

*Leaf length.*—12.8 cm.

*Leaf width.*—4.3 cm.

*Upper surface color.*—Dark green, uniform, no variegation; mature leaves near RHS 139 A; young leaves near RHS 139 A.

*Veins.*—Upper surface color dark red, RHS 53A; lower surface color dark red, about RHS 184 B (both young and mature leaves); veins on lower surface RHS 53 A.

*Petiole.*—5–15 mm in length, 3 mm in diameter.

*Petiole color.*—Upper side reddish, RHS 53 B to RHS 53 C, lower side RHS 53 A.

Inflorescence:

*Flowering response.*—9–10 weeks after planting of rooted cuttings.

*Flowering season.*—Generally from March to October, depending on light intensity.

*Flower.*—Flowers outwardly directed, borne well above the foliage canopy.

*Number of flowers per node.*—6–8, in various stages of development.

*Form of corolla.*—Single-type, 5 petals.

*Shape of corolla.*—Weakly zygomorphic, flat to faintly butterfly-shaped, with the petals overlapping.

*Corolla size.*—Average length: 69 mm. Average width: 65 mm. Depth: 10–15 mm.

*Shape of petals.*—Heart-shaped, slightly lobed at the top end.

*Size of petals.*—Top petal: 30 mm long, 50 mm wide. Lateral petals: 33 mm long, 40 mm wide. Lower petals: 33 mm long, 45 mm wide. Texture: Smooth, velvety. Aspect: Mostly flat.

*Color (general tonality from a distance of three meters).*—Bi-colored, almost white to pale bluish-pink ground color and bright red-purple markings, a large spot on the top petals and narrow radial stripes.

*Upper surface.*—Pale bluish-pink RHS 75 C to white, RHS 155 D.

*Color of markings.*—Red, between RHS 52 A and 57 A.

*Color of eye zone.*—Red-purple, RHS 57 A.

*Color of lower surface.*—RHS 58 B to RHS 58 C.

*Spur.*—Only one spur per flower, downwardly curved, about 50 mm in length, 3 mm in diameter at the flower end; pink, RHS 51 A.

*Peduncle.*—Color light green, RHS 145 B to RHS 145 C; length 65 mm.

*Flower bud.*—Ovoid, 22 cm in length, 17 mm in width; color RHS 58 B.

Reproductive organs:

*Stamens.*—Fused, 6 mm in diameter, upper surface color is mainly RHS 57 B.

*Anthers.*—5 in number, fused, hooded.

*Pollen.*—Whitish-yellow, about RHS 8 D.

*Style and stigma.*—Five in number, very short, reddish, about RHS 53 C.

*Ovary.*—5-celled, 5 mm long, brown.

Disease/pest resistance/susceptibility: No observation made to date.

I claim:

1. A new and distinct cultivar of New Guinea *Impatiens* plant named 'Fisupnic Chersweet', as described and illustrated herein.

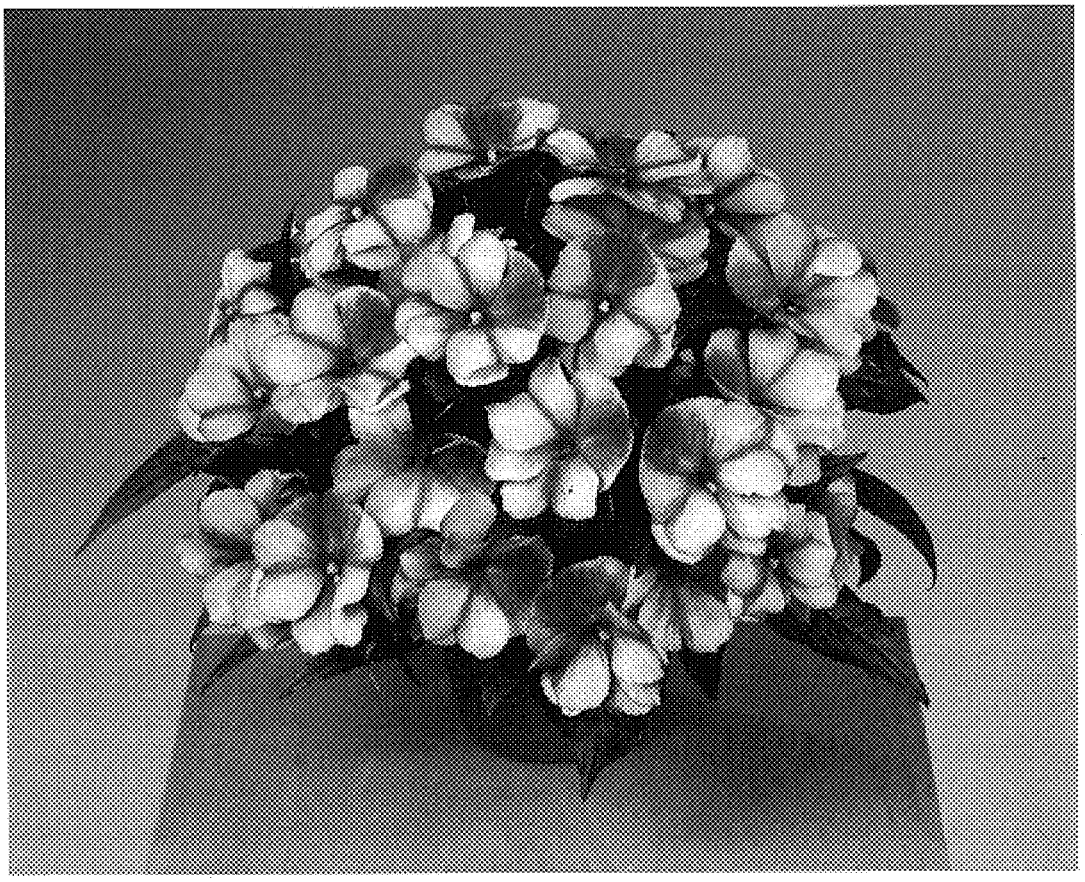

* * * * *